(12) United States Patent
Bruggeman

(10) Patent No.: US 8,962,683 B2
(45) Date of Patent: Feb. 24, 2015

(54) MEDIUM CHAIN FATTY ACIDS APPLICABLE AS ANTI-MICROBIAL AGENTS

(75) Inventor: Geert Bruggeman, Bruges (BE)

(73) Assignee: Nutrition Sciences NV, Drongen (BE)

( * ) Notice: Subject to any disclaimer, the term of this patent is extended or adjusted under 35 U.S.C. 154(b) by 2258 days.

(21) Appl. No.: 11/630,536

(22) PCT Filed: Jun. 30, 2005

(86) PCT No.: PCT/EP2005/007067
§ 371 (c)(1),
(2), (4) Date: Dec. 21, 2006

(87) PCT Pub. No.: WO2006/002927
PCT Pub. Date: Jan. 12, 2006

(65) Prior Publication Data
US 2007/0219270 A1    Sep. 20, 2007

(30) Foreign Application Priority Data

Jun. 30, 2004  (WO) ................. PCT/EP2004/007106

(51) Int. Cl.
| | |
|---|---|
| *A61K 31/20* | (2006.01) |
| *A23K 1/16* | (2006.01) |
| *A23K 1/18* | (2006.01) |
| *A23L 1/30* | (2006.01) |
| *A61K 31/19* | (2006.01) |

(52) U.S. Cl.
CPC ............... *A23K 1/164* (2013.01); *A23K 1/1826* (2013.01); *A23K 1/184* (2013.01); *A23L 1/3006* (2013.01); *A61K 31/19* (2013.01); *A61K 31/20* (2013.01); *A23V 2002/00* (2013.01)
USPC ....................................................... 514/558

(58) Field of Classification Search
CPC ...................................................... A61K 31/20
USPC ........................................................ 514/558
See application file for complete search history.

(56) References Cited

U.S. PATENT DOCUMENTS

| | | | |
|---|---|---|---|
| 4,489,097 A | 12/1984 | Stone | |
| 5,234,703 A | 8/1993 | Guthery | |
| 5,460,802 A * | 10/1995 | Asami et al. | 424/49 |
| 5,569,461 A | 10/1996 | Andrews | |
| 6,638,978 B1 * | 10/2003 | Kabara | 514/550 |
| 2003/0157159 A1 | 8/2003 | Franklin et al. | |

FOREIGN PATENT DOCUMENTS

| | | |
|---|---|---|
| DE | 12 50 423 C | 9/1967 |
| EP | 0089376 A1 * | 9/1982 |
| EP | 0519458 A1 * | 12/1992 |
| EP | 0 713 700 A1 | 5/1996 |
| GB | 1 582 992 | 1/1981 |
| JP | 2002370921 A | 12/2002 |
| WO | WO 95/25513 | 9/1995 |
| WO | WO 98/09520 | 3/1998 |
| WO | WO 01/97799 A1 | 12/2001 |
| WO | WO 02/056879 A1 | 7/2002 |
| WO | WO 03/063619 A1 | 8/2003 |

OTHER PUBLICATIONS

Petschow et al. Impact of medicum-chain monoglycerides on intestinal colonisation by *Vibro cholerae* or enterotoxigenic *Escherichia coli*. J. Med. Microbiol. vol. 47 (1998), pp. 383-389.*

Marounck et al., "Susceptibility of *Escherichia coli* to C2-C18 Fatty Acids." Abstract: Folia Microbiol. (Praha) 2003; 48:731-5.

Sprong R C et al., entitled "Bovine milk fat components inhibit food-borne pathogens," International Dairy Journal, 12 (2002), pp. 209-215.

Sprong R C et al, entitled "Bactericidal Activities of Mile Lipids," Antimicrobial Agents and Chemotherapy, Apr. 2001, vol. 45, pp. 1298-1301.

Lin J et al., entitled "Critical Role of Multidrug Efflux Pump CmeABC in Bile Resistance and In Vivo Colonization of *Campylobacter jejuni*," Infection and Immunity, Aug. 2003, vol. 71, pp. 4250-4259.

* cited by examiner

*Primary Examiner* — Jennifer M Kim
(74) *Attorney, Agent, or Firm* — Amster, Rothstein & Ebenstein LLP

(57) ABSTRACT

The present invention relates to the use of medium chain fatty acids (MCFA), chosen from the group consisting of caproic acid ($C_6$), caprylic acid ($C_8$) and capric acid ($C_{10}$), salts, derivatives or mixtures thereof, in a total amount by weight comprised between 0.01% and 5% for inhibiting the growth of microbial pathogens.

11 Claims, 6 Drawing Sheets

US 8,962,683 B2

MEDIUM CHAIN FATTY ACIDS APPLICABLE AS ANTI-MICROBIAL AGENTS

This is a U.S. national phase of PCT Application No. PCT/EP2005/007067, filed Jun. 30, 2005 and claims priority to PCT Application No. PCT/EP2004/007106, filed Jun. 30, 2004.

TECHNICAL FIELD

The present invention relates to the use of medium chain fatty acids (MCFA) or their salts or derivatives thereof or mixtures thereof as specific inhibitors of microbial contamination and growth. In particular, the present invention relates to the use of caproic ($C_6$), caprylic ($C_8$) and capric ($C_{10}$) acids, salts, derivatives or mixtures thereof to inhibit the growth of food-born microbial pathogens, especially *Campylobacter* sp. *Salmonella* sp., *Escherichia* sp. and *Enterococcus* sp.

BACKGROUND OF THE INVENTION

Microbial strains of importance for animal and human health are *Campylobacter* sp., *Salmonella* sp., *Escherichia coli*, moulds, etc. . . . As an example, *Campylobacter* is actually among world's most common human enteropathogens, causing campylobacteriosis. Campylobacteriosis is now the major zoonotic cause of human inflammatory intestinal infection, followed by salmonellosis and listeriosis. The clinical spectrum of enteric diseases due to *Campylobacter* infection ranges from generally mild non-inflammatory diarrhoea to severe inflammatory diarrhoea with faecal blood and leucocytes (Scott et al., 1997; Friedman et al., 2000; Oberhelman and Taylor, 2000).

The reported European incidence for human campylobacteriosis varies from 9.5 cases annually per 100,000 habitants in Spain to 108 cases annually per 100,000 in Scotland. The calculation may be underestimated since many cases are not reported and diagnostic tools vary in different countries. The incidence is still increasing in most European countries.

*Campylobacter* is also one of the most common bacterial causes of diarrhoeal illness in the United States. Virtually all cases occur as isolated, sporadic events, not as a part of large outbreaks. Active surveillance through US FoodNet indicates about 15 cases are diagnosed each year for each 100,000 persons. Many more cases go undiagnosed or unreported, and campylobacteriosis is estimated to affect over 1 million persons every year, or 0.5% of the general population.

In addition, *Campylobacter* infections are also linked to the Guillain-Barré Syndrome and arthritis (Scott et al., 1997; Nachamkin et al., 1998). The mortality associated with *Campylobacter* infections is relatively low and no specific treatment is required for the great majority of patients. Although *Campylobacter* doesn't commonly cause death, it has been estimated that approximately 100 persons with *Campylobacter* infections may die every year. However, *Campylobacter* infections are nevertheless serious problems because of high number of cases and their neurological symptoms, as well as the high social and economic costs of disease. The community pays a high economical cost due to loss of working hours, medical and treatment costs (mainly by use of fluoroquinolones and macrolides). Additionally, systemic infections do occur specially in elderly patients or in patients that are immunocompromised such as HIV-infected individuals. As the average lifetime of Europeans has been increasing consistently, one can expect more serious complications of *Campylobacter* infections particularly in cases involving old patients.

The problem with increasing or continued high incidence of human food-born infections cannot be solved on the basis of present knowledge. Maintaining increased hygiene standards have had an impact on salmonellosis but not on campylobacteriosis. Existing knowledge does not solve these problems, since there is lack of understanding the mechanisms by which zoonotic bacteria invade and infect (Scott et al., 1997; Oberhelman and Taylor, 2000; Newell and Nachamkin, 1992).

Outbreaks of campylobacteriosis are frequently traced to contaminated milk or water, whereas the most common cause of sporadic cases is eating undercooked meat, e.g. poultry. Contaminated chickens are, by far, the principal vehicles of infection (Friedman et al., 2000; Corry and Atabay, 2001; Newell and Wagenaar, 2000).

Poultry are a major reservoir of *Campylobacter jejuni* where the bacteria persist within the gastrointestinal tract. The epidemiology of *C. jejuni* in broiler flocks is still unclear. Generally, birds become infected about 3 weeks of age, but the sources and the routes of transmission of the microorganism to the broilers on the farm remain undetermined. Recently obtained data have indicated several sources of infection, including water, wild birds and farm personnel (Corry and Atabay, 2001). Once the microorganism is introduced in the flock, it spreads very rapidly leading to infection of almost all birds in a very short time. Although the reported level of *Campylobacter* in the chickens ceca varies between $10^5$ and $10^{10}$/g, this massive colonisation does not induce any sign of the disease. The high amount of *Campylobacter* in the birds faeces causes further cross-contamination of *Campylobacter*-negative chicken carcasses in the processing plants. As a result, *Campylobacter* contaminates 50-80% of the raw chicken carcasses, depending on the geographical region where the study was conducted and the method used. This fact, in combination with the relatively low human infection dose can explain why eating undercooked poultry causes the majority of sporadic cases of campylobacteriosis. Therefore, one of the challenges is to understand how to block or diminish intestinal colonisation by *Campylobacter* in the host zoonotic animals, e.g. poultry.

Current methods of hygiene and bio-security used are improvement of the bio-security in the hatchery, a competitive exclusion technology or using chlorinated water (Corry and Atabay, 2001; Newell and Wagenaar, 2000). But they are insufficient to control or eliminate *Campylobacter* from the poultry food chain. Another strategy concerns preventive dosing of antibiotics (growth promoters) to the animals. However, concerns over potential health risk of antibiotic residues and resistant strains of pathogenic bacteria from animal sources have increased over the years and there are increasing pressures on the regulatory bodies to ban the use of these growth promoters (Barton, 1998; Dupont and Steele, 1987; Guillot, 1989; Prescott, 1997). Therefore, a total ban of antibiotics is foreseen for end 2005. Finally, another alternative approach for control of *Campylobacter* contamination can be active immunization of the birds. However, at the moment there is limited information about the function of the chicken immune system. Although some international research institutes are dealing with this topic, a real break-trough of this technique is for far future.

Therefore, alternative approaches for controlling food-born pathogens and other microbial contamination—in casu *Campylobacter* sp., *Salmonella* sp., *Escherichia coli*, etc. . . .—are urgently needed.

It is an object of the present invention to provide an alternative approach for controlling the amount and growth of food-born pathogens and other microbial contamination.

In particular, the present invention aims to provide compositions and methods for reducing the amount and/or growth of food-born pathogens and microbial organisms in consumable (edible) products. Another object of the invention is to provide compositions and methods for reducing the amount and/or growth of food-born pathogens and microbial organisms in animals or humans. The present invention is based on the use of specific medium chain fatty acids (MCFA) and in particular caproic acid ($C_6$), caprylic acid ($C_8$), and capric acid ($C_{10}$), salts, derivatives or mixtures thereof, for the control of microbial contamination and growth.

SUMMARY

The present invention is directed to the use of medium chain fatty acids (MCFA), chosen from the group consisting of caproic acid ($C_6$) caprylic acid ($C_8$), and capric acid ($C_{10}$), salts, derivatives or mixtures thereof, for inhibiting the growth of microbial pathogens, in particular for inhibiting the growth of food-born pathogens. The present invention relates to the observation that specific medium chain fatty acids $C_6$ and/or $C_8$, and/or $C_{10}$, their salts or derivatives or mixtures as a solution or in an emulsion to have anti-microbial effects on microbial pathogens and permit to inhibit further growth of these microbial pathogens, and to substantially reduce their amounts. These pathogens merely comprise bacteria such as, but not limited to, *Campylobacter* sp., *Salmonella* sp., *Escherichia coli*, *Enterococcus* sp.

In a first aspect, the present invention therefore relates to the use of medium chain fatty acids (MCFA), chosen from the group consisting of caproic acid ($C_6$), caprylic acid ($C_8$), capric acid ($C_{10}$), salts, derivatives or mixtures thereof, in a total amount by weight which is lower than 5% and preferably comprised between 0.01% and 5% for inhibiting the growth and/or for reducing the amount of microbial pathogens. More in particular, the MCFA are used in a total amount by weight comprised between 0.01% and 5%, preferably between 0.05% and 5%, preferably between 0.1% and 2.5%, more preferably between 0.25% and 1.5%, and most preferably in an amount by weight of 0.3% for inhibiting the growth of microbial pathogens.

The use of these amounts of $C_6$ and/or $C_8$ and/or $C_{10}$ MCFA not only permits to inhibit the growth of microbial pathogens but also permits to kill food-born pathogens. Surprisingly these small amounts of specific MCFA are sufficient to provide good anti-microbial effect without having substantial adverse and/or harmful effects on the microbial flora in the gastrointestinal tract.

In the present invention, preferably use is made of a mixture of specific different fatty acids. The Applicant has found that such a mixture shows optimal antimicrobial properties against microbial strains.

In a particular preferred embodiment, the MCFA are used as free fatty acids, or as a mixture of one or more of their salts or derivatives, to prevent the composition from spreading an unpleasant odour. The fatty acids that can be used in this invention include fatty acids with an even number of carbon atoms. In a preferred embodiment, the used MCFA comprise a mixture of $C_6$ (caproic acid, hexanoic acid) and $C_8$ (caprylic acid, octanoic acid), a mixture of $C_8$ and $C_{10}$ (capric acid, decanoic acid), a mixture of $C_6$ and $C_{10}$, or a mixture of $C_6$, $C_8$ and $C_{10}$ MCFA.

The antimicrobial effects of fatty acids and their salts have already been known for a long time and have been reviewed by J. J. Kabara (1978) in "The pharmacological effects of lipids". In this review it is discussed that in homologous series of fatty acids, the bactericidal efficiency has been found to increase with increasing chain length. *E. coli* spp. and *Shigella* spp. appear to be killed by moderate concentrations of saturated soaps of lauric acid containing 12 carbon atoms, and stearyl fatty acid containing 18 carbon atoms. Fatty acids with a chain length of about 12 carbon atoms appear to show optimal antimicrobial activity, whereas lower fatty acids with 4-10 carbon atoms appear to have no or little germicidal effect.

The mechanism according to which the fatty acids exert antimicrobial activity has been well documented in literature. The currently accepted theory is that the lipid microbial cell membrane is permeable for the undissociated fatty acid, as a consequence of which the fatty acid is capable of passing across the microbial cell membrane towards the more alkaline interior. Because of the higher intracellular alkalinity, the fatty acid is dissociated, thus involving a decrease of the intracellular pH below the survival level. The fatty acid thus in fact acts as a protonophore, which increases inward leak of $H^+$ and involves that efflux of $H^+$ is too slow to allow the intracellular pH to be increased again. The physicochemical properties of the fatty acids which allow them to act as protonophores, may vary and depend on numerous parameters. Examples of such parameters are the chain length and pKa of the fatty acid, as well as the physicochemical environment, precipitations, the pH at the place of action and the chemical composition of the microbial envelope, which determines the passage of the fatty acids through the membrane.

In this respect, the better performance of the fatty acid containing $C_6$ and/or $C_8$ and/or $C_{10}$ carbon atoms is attributed to the extreme permeability of the microbial cell membrane for this fatty acid. This is unexpected, since Kabara (1978) discloses that lower fatty acids containing 4-10 carbon atoms show little germicidal activity. An increase of the pH from 6.5 to 7.5 increased the minimum inhibitory concentration of the short chain fatty acids containing 6-8 carbon atoms, and decreased the minimum concentrations of the two MCFA containing 12-14 carbon atoms (lauric, myristic acid).

There is however no teaching in Kabara (1978) that fatty acids containing $C_6$ and/or $C_8$ and/or $C_{10}$ carbon atoms would be capable of controlling and even inhibiting microbial growth.

This particular antimicrobial action of the above mentioned specific MCFA ($C_6$ and/or $C_8$ and/or $C_{10}$) in the above-given concentrations has not been described previously for microbial strains. By inhibition of growth and by killing the microbial pathogens, the respective microbial pathogens are not able anymore to cause cell intrinsic diseases.

Conclusive, $C_6$, $C_8$ and $C_{10}$ MCFA, or their salts or derivatives or mixtures thereof, inhibit the growth of food-born pathogens, in particular by killing the pathogens. The invention provides for the use of a specific small range of MCFA ($C_6$ and/or $C_8$ and/or $C_{10}$) at the above-mentioned low concentrations as anti-microbial agents. This specific range permits to inhibit outgrowth of food born pathogens by killing the microbial cells.

Possible uses are all situations where microbial contamination is disadvantageous and must be monitored and controlled. For this reason, the specific MCFA can be applied in powdered and liquid foods and feeds, in human healthcare (e.g. in case of diarrhoea), in food and feed preservation (fruit, cheese, cake, bread, etc. . . . ), in drinks, in cleaning (disinfecting) agents and detergents, etc. . . . As a result, microbial growth can be controlled in a more friendly way, compared to the use of traditional compounds such as growth promoters, antibiotics, etc.

Hereunder several examples prove the antimicrobial effectiveness of use of $C_6$ and/or $C_8$ and/or $C_{10}$ MCFA at the above-mentioned concentrations as anti-microbial agents. It is clear that these examples will have an explanatory goal and are not limitative to the scope of the invention, which is worded in the claims.

DETAILED DESCRIPTION OF THE INVENTION

Figure 1:
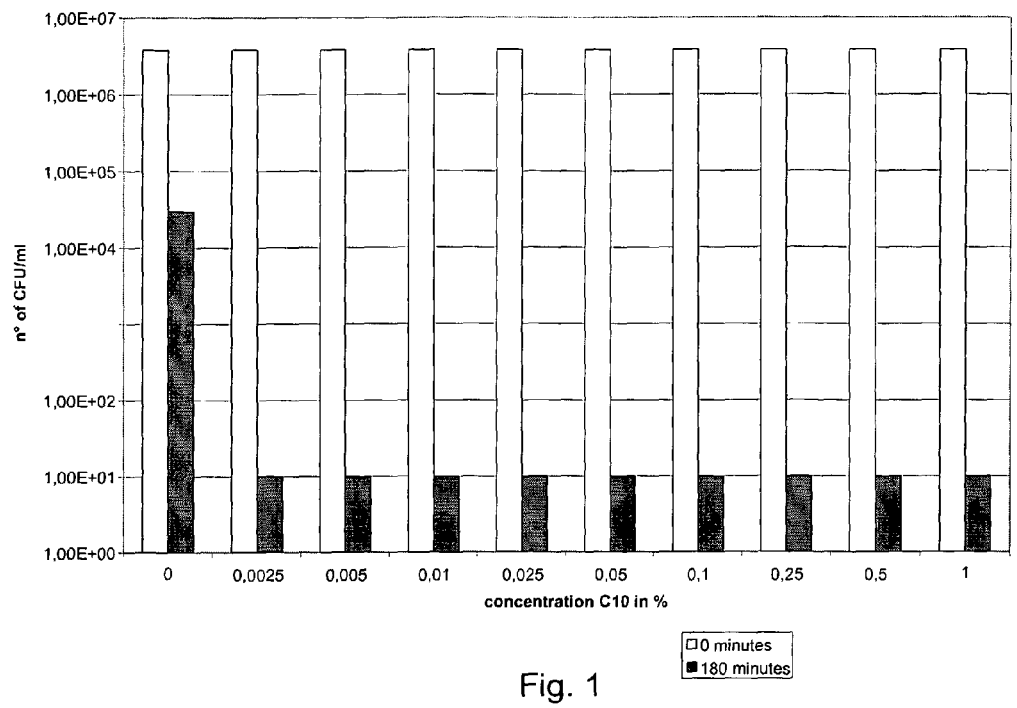
FIGS. 1 to 3 illustrate the effect of $C_{10}$ MCFA on growth and survival of different *Campylobacter* sp. strains isolated from poultry caecum.

In a first embodiment, the present invention relates to the use of medium chain fatty acids (MCFA), chosen from the group consisting of caproic acid ($C_6$) and caprylic acid ($C_8$), and capric acid ($C_{10}$), salts, derivatives or mixtures thereof, for inhibiting the growth and/or for reducing the amount of microbial pathogens, in particular for inhibiting the growth and/or for reducing the amount of food-born pathogens.

In a particularly preferred embodiment, the present invention is directed to the use of medium chain fatty acids (MCFA), chosen from the group consisting of caproic acid ($C_6$) and caprylic acid ($C_8$), and capric acid ($C_{10}$), salts, derivatives or mixtures thereof, for reducing the amount of microbial pathogens with more than 25%, and preferably more than 50%, and even more preferred with more than 75% and preferably up to 100%.

The term "microbial pathogens" as used herein refers to micro-organisms that have a pathogenic character, i.e. that are able to cause a disease or disorder in animals and/or humans.

The term "food-born pathogens" as used herein refers to microbial pathogens which contaminate food or feed. These pathogens merely comprise bacteria such as, but not limited to, *Campylobacter, Salmonella, Escherichia coli, Enterococcus*.

As used herein, the term "MCFA" refers to a medium chain fatty acid wherein said "medium chain fatty acid" means a saturated fatty acid, unsaturated fatty acid, or mixture thereof, having 6 to 10 carbon atoms. By "medium chain saturated fatty acid," as used herein, is meant $C_6$ (caproic), $C_8$ (caprylic), $C_{10}$ (capric), or any mixtures thereof.

As used herein, the term "MCFA salt" refers to a salt of the free fatty acid. As used herein, the term "free fatty acid" refers to an underivatised fatty acid, i.e. a fatty acid not converted into a salt, an amide, an ester etc.

As used herein, the term "MCFA derivative" refers to a medium chain fatty acid whose carboxylic acid group is reversibly converted into another group to form amides, esters, glycerides. In this specification, the term MCFA derivative excludes MCFA salt.

In particular, the invention relates to the use of medium chain fatty acids (MCFA), chosen from the group consisting of caproic acid ($C_6$) caprylic acid ($C_8$) and capric acid ($C_{10}$), salts, derivatives or mixtures thereof, for inhibiting the growth of *Campylobacter jejuni, Campylobacter coli, Campylobacter laris, Campylobacter upsaliensis*, and/or other *Campylobacter* sp.

In another particular embodiment, the invention relates to the use of medium chain fatty acids (MCFA), chosen from the group consisting of caproic acid ($C_6$) caprylic acid ($C_8$), and capric acid ($C_{10}$), salts, derivatives or mixtures thereof, for inhibiting the growth of *Salmonella typhimurium, Salmonella enteritidis* and/or *Salmonella java*.

In one embodiment, the invention is directed to the use of medium chain fatty acids (MCFA), chosen from the group consisting of caproic acid ($C_6$), caprylic acid ($C_8$), capric acid ($C_{10}$), salts, derivatives or mixtures thereof, in a total amount by weight which is lower than 5%, and preferably lower than 3%, lower than 1%, or even lower than 0.1% for inhibiting the growth and/or for reducing the amount of microbial pathogens.

In a preferred embodiment, caproic acid ($C_6$), salts or derivatives thereof are used in an amount by weight comprised between 0.01% and 5%, preferably between 0.05% and 5%, preferably between 0.1% and 2.5%, more preferably between 0.25% and 1.5%, and most preferably in an amount by weight of 0.3%. In another preferred embodiment, caprylic acid ($C_8$), salts or derivatives thereof are used in an amount by weight comprised between 0.01% and 5%, preferably between 0.05% and 5%, preferably between 0.1% and 2.5%, more preferably between 0.25% and 1.5%, and most preferably in an amount by weight of 0.3%. In yet another preferred embodiment, capric acid ($C_{10}$), salts or derivatives thereof are used in an amount by weight comprised between 0.01% and 5%, preferably between 0.05% and 5%, preferably between 0.1% and 2.5%, more preferably between 0.25% and 1.5%, and most preferably in an amount by weight of 0.3%.

In yet another preferred embodiment, a mixture of caproic acid ($C_6$) and caprylic acid ($C_8$) is used. The use of a mixture of caprylic acid ($C_8$) and capric acid ($C_{10}$) is also encompassed by the present invention. In yet another preferred embodiment, a mixture of caproic acid ($C_6$) and capric acid ($C_{10}$) is used. Also, in another embodiment, the invention may relate to the use of a mixture of caproic acid ($C_6$) caprylic acid ($C_8$) and capric acid ($C_{10}$).

Various mixtures of caproic acid ($C_6$) caprylic acid ($C_8$) and capric acid ($C_{10}$) MCFA, and relative ratios of the MCFA in such mixtures, may be used in the present invention. Preferably the ratio of $C_6$ to $C_8$ in a $C_6/C_8$ mixture is comprised between 2:1 and 1:2 and preferably comprises 1:1. In another preferred embodiment, the ratio of $C_8$ to $C_{10}$ in a $C_8/C_{10}$ mixture is comprised between 2:1 and 1:2 and preferably comprises 1:1. In yet another embodiment, the ratio of $C_6$ to $C_{10}$ in a $C_6/C_{10}$ mixture is comprised between 2:1 and 1:2 and preferably comprises 1:1. In still another preferred embodiment, the ratio of $C_6$ to $C_8$ to $C_{10}$ in a $C_6/C_8/C_{10}$ mixture may be 1:1:2 or 1:2:1 or 2:1:1 or 1:2:2 or 2:1:2 or 2:2:1 or 1:1:1 and preferably comprises 1:1:1.

In a preferred embodiment, caproic acid ($C_6$) and caprylic acid ($C_8$) are used in about equal amounts by weight. Preferably, caproic acid ($C_6$) and caprylic acid ($C_8$) are used in a total amount by weight comprised between 0.01% and 5%, preferably between 0.05% and 5%, preferably between 0.1% and 2.5%, more preferably between 0.25% and 1.5%, and most preferably in an amount by weight of 0.3%.

The present invention also relates in another preferred embodiment, to the use of caprylic acid ($C_8$) and capric acid ($C_{10}$) in about equal amounts by weight. Preferably, caprylic acid ($C_8$) and capric acid ($C_{10}$) are used in a total amount by weight comprised between 0.01% and 5%, preferably between 0.05% and 5%, preferably between 0.1% and 2.5%, more preferably between 0.25% and 1.5%, and most preferably in an amount by weight of 0.3%.

In another preferred embodiment, caproic acid ($C_6$) and capric acid ($C_{10}$) are used in about equal amounts by weight. Preferably, caproic acid ($C_6$) and capric acid ($C_{10}$) are used in a total amount by weight comprised between 0.01% and 5%, preferably between 0.05% and 5%, preferably between 0.1% and 2.5%, more preferably between 0.25% and 1.5%, and most preferably in an amount by weight of 0.3%.

In another preferred embodiment, caproic acid ($C_6$), caprylic acid ($C_8$), and capric acid ($C_{10}$) are used in about equal amounts by weight. Preferably, caproic acid ($C_6$), caprylic acid ($C_8$), and capric acid ($C_{10}$) are used in a total amount by weight comprised between 0.01% and 5%, preferably between 0.05% and 5%, preferably between 0.1% and 2.5%, more preferably between 0.25% and 1.5%, and most preferably in an amount by weight of 0.3%.

In yet another embodiment, the MCFA are used as crafted MCFA. The term "crafted MCFA" as used herein refers to an MCFA molecule which has a chemical side-group such as an alkyl group, preferably a C1-C10 alkyl, and for instance a methyl or ethyl group. In a preferred embodiment, the MCFA are methyl-, ethyl-, derivatives or other crafted derivatives.

In another embodiment, the MCFA used in accordance with the present invention may be used in various forms. For instance, the invention may relate to the use of MCFA as defined herein, wherein the MCFA as used as free MCFA, as mono-, di- and/or triglicerides, as $NH_4^+$—, $Na^+$—, $K^+$— and/or $Ca^{2+}$— salts or in the form of an emulsion.

In a further embodiment, the MCFA are used in combination with other MCFA, such as lauric ($C_{12}$) and myristic ($C_{14}$) acid, other antifungal agents or with other (organic or inorganic) (fatty) acids or with additives, such as aroma's and plant extracts.

Examples of other organic acids include but are not limited to $C_{1-12}$ carboxylic acids selected from the group comprising unsubstituted carboxylic acids such as formic acid, acetic acid, propionic acid, butyric acid, valerianic acid, and caproic acid, substituted carboxylic acids such as adipic acid, maleic acid, succinic acid, citric acid, fumaric acid, tartaric acid, lactic acid, gluconic acid, malic acid, and ascorbic acid, including cyclic carboxylic acids such as picolinic acid. The organic acid component may be a single unsubstituted carboxylic acid, a single substituted carboxylic acid, a mixture of unsubstituted carboxylic acids, a mixture of substituted carboxylic acids and a mixture of unsubstituted carboxylic acids and substituted carboxylic acids including saturated, unsaturated, cyclic and aliphatic carboxylic acids and metal complexes and salts thereof. Also single racemic forms and racemic mixtures may be used.

Examples of inorganic acids include but are not limited to strong inorganic acids in small quantities such as perchloric acid, hydroiodic acid, hydrobromic acid, hydrochloric acid, sulfuric acid, and nitric acid and weak inorganic acids such as phosphoric acid, hydrofluoric acid, hypochlorous acid, and nitrous acid.

A further aspect of the present invention relates to the use of medium chain fatty acids (MCFA), chosen from the group consisting of caproic acid ($C_6$), caprylic acid ($C_8$), and capric acid ($C_{10}$), salts, derivatives or mixtures thereof, preferably in a total amount by weight which is lower than 5% and preferably comprised between 0.01% and 5%, preferably between 0.05% and 5%, preferably between 0.1% and 2.5%, more preferably between 0.25% and 1.5%, and most preferably in an amount by weight of 0.3% for as an additive for food or feed preservation.

In another aspect, the present invention relates to the use of medium chain fatty acids (MCFA), chosen from the group consisting of caproic acid ($C_6$), caprylic acid ($C_8$), and capric acid ($C_{10}$), salts, derivatives or mixtures thereof, preferably in a total amount by weight which is lower than 5%, and preferably comprised between 0.01% and 5%, preferably between 0.05% and 5%, preferably between 0.1% and 2.5%, more preferably between 0.25% and 1.5%, and most preferably in an amount by weight of 0.3% for the control and regulation of the microbial ecosystem in the gastrointestinal tract of any animal or human.

In yet another aspect, the present invention relates to an edible composition for inhibiting the growth and/or for reducing the amount of microbial pathogens comprising a feed supplement containing medium chain fatty acids (MCFA) chosen from the group consisting of caproic acid ($C_6$), caprylic acid ($C_8$), and capric acid ($C_{10}$), salts, derivatives or mixtures thereof, whereby said MCFA are present in the feed supplement in a total amount by weight which is lower than 5%, and preferably comprised between 0.01% and 5%, preferably between 0.05% and 5%, preferably between 0.1% and 2.5%, more preferably between 0.25% and 1.5%, and most preferably in an amount by weight of 0.3%.

The term "edible composition" according to the invention is to be construed as being a feed of food, and thus consumable by an animal or human.

The term "feed supplement" as used herein refers to a substance that has been added in small amounts to the edible composition to improve said composition, and is also to be understood as being suitable for consumption by an animal or human.

In a particularly preferred embodiment, the present composition is capable of reducing the amount of microbial pathogens with more than 25%, and preferably with more than 50%, and even more preferred with more than 75% and preferably up to 100%.

The MCFA present in the composition may present in the type of mixtures, ratios, amounts and in the formulation types as indicated above. Preferably, the composition comprises a feed supplement wherein a mixture of $C_6$ and $C_8$ is used, wherein a mixture of $C_8$ and $C_{10}$ is used, wherein a mixture of $C_6$ and $C_{10}$ is used, wherein a mixture of $C_6$, $C_8$, and $C_{10}$ is used.

More preferably, the composition comprises a feed supplement wherein caproic acid ($C_6$) and caprylic acid ($C_8$) are present in about equal amounts by weight, and preferably in an amount by weight comprised between 0.01% and 5%, preferably between 0.05% and 5%, preferably between 0.1% and 2.5%, more preferably between 0.25% and 1.5%, and most preferably in an amount by weight of 0.3%. In yet another embodiment, the composition comprises a feed supplement wherein caprylic acid ($C_8$) and capric acid ($C_{10}$) are present in about equal amounts by weight, and preferably in an amount by weight comprised between 0.01% and 5%, preferably between 0.05% and 5%, preferably between 0.1% and 2.5%, more preferably between 0.25% and 1.5%, and most preferably in an amount by weight of 0.3%. In still another embodiment, the composition comprises a feed supplement wherein caproic acid ($C_6$) and capric acid ($C_{10}$) are present in about equal amounts by weight, and preferably in an amount by weight comprised between 0.01% and 5%, preferably between 0.05% and 5%, preferably between 0.1% and 2.5%, more preferably between 0.25% and 1.5%, and most preferably in an amount by weight of 0.3%. In yet another embodiment, the composition comprises a feed supplement wherein caproic acid ($C_6$), caprylic acid ($C_8$) and capric acid ($C_{10}$) are present in about equal amounts by weight, and preferably in an amount by weight comprised between 0.01% and 5%, preferably between 0.05% and 5%, preferably between 0.1% and 2.5%, more preferably between 0.25% and 1.5%, and most preferably in an amount by weight of 0.3%.

In another preferred embodiment, the MCFA concentration in the composition comprises between 100-3000 ppm, preferably between 300 and 2000 ppm, preferably between 500 and 1500 ppm and even more preferably around 1200 ppm.

In yet another embodiment, the invention provides a composition containing an effective amount of A) a first MCFA selected from the group consisting of caproic acid ($C_6$), caprylic acid ($C_8$), and capric acid ($C_{10}$), salts, derivatives thereof, whereby said MCFA is preferably present in an amount by weight which is lower than 5%, and B) an effective amount of a second MCFA selected from the group consisting of caproic acid ($C_6$), caprylic acid ($C_8$), and capric acid ($C_{10}$), salts, derivatives thereof, whereby said MCFA is preferably present in an amount by weight which is lower than 5%, as a combined preparation for simultaneous, separate or sequential use for inhibiting the growth and/or for reducing the amount of microbial pathogens According to the present invention, a composition is provided for use as feed for meat-producing animals. As herein used, the term "animals" refer to livestock animals including but not limited to cattle such as ruminants, sheep, swine including pigs and hogs, horses, and poultry, and their progeny, such as sucking pigs, piglets, calves, lambs kids, foals and chickens etc. Also fishes, such as eel, carps, trout, rainbow trout, yellowtail, sea bream, silver salmon, gold fishes, colored carp, tropical fishes; shellfishes; crustaceans; are examples of the animals covered by the composition of the present invention. Also pets, such as dogs, cats, rabbits, hamsters, and their progeny are examples of the animals covered by the composition of the present invention. According to yet another embodiment of the present invention, a composition is provided for use as feed for milk-producing animals such as but not limited to cows, sheep, goats, horses, etc. . . .

The present composition permits to stimulate a good-functioning and well-balanced microbial ecosystem in the gastrointestinal tract of an animal. Control of the microbial ecosystem in the gastrointestinal tract of an animal permits to obtain better performances and improves health and wellbeing of the animals. Better performances are reflected in a better daily weight gain and a lower feed conversion rate in growing animals. The term "feed conversion" is used to describe efficiency in animal feed uptake and refers to the units of feed consumed divided by the units of animal weight gain over a specific time period. The "Feed Conversion Ratio" is the ratio of the amount of feed consumed relative to the weight gain of an animal. Use of a specific range of MCFA in the above-mentioned concentrations according to the present invention thus improves feed conversion activities of animals without concomitant substantial or significant stimulation of feed intake. As used herein the expression "improving the feed conversion" and cognate expressions such as "feed conversion improvement" refer to improving feed utilization efficiency and/or improving growth rate. That is, in accordance with the present invention, treated animals (as compared to untreated animals) can have substantially the same feed intake and grow at an increased growth rate, can have decreased feed intake and grow at substantially the same growth rate, or can have decreased feed intake and grow at an increased growth rate. The term "growth" as used herein refers to a gain in weight.

In human being, control of the microbial ecosystem in the gastrointestinal tract also enables to improve health and wellbeing. More in particular, it permits to lower the risk of zoonotic microbial diseases such as campylobacteriosis, salmonelliosis, etc. in human beings.

Therefore, in another embodiment, the present invention also relates to a method for inhibiting the growth and/or for reducing the amount of microbial pathogens, preferably selected from the group comprising *Escherichia coli, Salmonella* sp., *Campylobacter* sp., and *Enterococcus* sp., in an animal or human, comprising administering to said animal or human an effective amount of a composition as defined herein.

In addition, the present composition permits to control the amount of microbial pathogens in edible products which as obtained from an animal. Therefore, in another embodiment, the present invention also relates to a method for inhibiting the growth and/or for reducing the amount of microbial pathogens, preferably selected from the group comprising *Escherichia coli, Salmonella* sp., *Campylobacter* sp., and *Enterococcus* sp., in an edible product obtained from an animal, comprising administering to said animal an effective amount of a composition as defined herein.

The term "edible product" as used herein comprises a product that is obtained from an animal and that is consumable and digestible, such as for instance milk, meat, eggs, cheese, cream, butter, etc. . . . but also any product further prepared using these edible products as ingredient.

The present method involves the control of the microbial ecosystem in the gastrointestinal tract of an animal and the reduction of the amount of microbial pathogens in the animal. As a consequence thereof, the number of animals contaminated with microbial pathogens and/or their contamination degree can be reduced, and entry of the microbial pathogens in the food chain and further cross-contamination in the processing plants can be significantly reduced.

The following examples are meant to illustrate the present the invention and should not be taken as limiting in any way.

EXAMPLES

Example 1

Influence of MCFA on Growth and Survival of *C. Jejuni* and *C. Coli*.

Eight *Campylobacter* strains were included in this study. Two strains (*C. jejuni* LMG 6444$^T$/ATCC 33560 and *C. coli* LMG 6440$^T$/ATCC 33559) were obtained from the BCCM™/LMG Bacteria Collection (Ghent University, Ghent, Belgium). Six unrelated *Campylobacter* strains (5 *C. jejuni* and 1 *C. coli*), isolated from Belgian poultry products and identified at species-level by multiplex-PCR were also tested in this study. Three antibiogram control strains, *S. aureus* ATCC 25922, *E. faecalis* ATCC 29212 and *E. coli* ATCC 25923 were tested as well.

Three tenfold dilutions of a 10% suspension of the MCFA product ($C_6$ and $C_8$) were prepared in distilled water. $C_6$ and $C_8$ were used in equal amounts (50/50) by weight. The 10% suspension thus contains 5% $C_6$ and 5% $C_8$. To obtain the desired concentrations, 1.5, 0.75 and 0.36 ml of these dilutions were pipetted in petri dishes and carefully mixed with 15 ml molten growth medium. The media used was Mueller-Hinton II medium (BBL) with a pH 7.2.

The *Campylobacter* strains were grown in Brian Heart infusion broth and incubated at 37° C. under micro-aerobic conditions by evacuating 80% of the normal atmosphere and introducing a gas mixture of 8% $CO_2$, 8% $H_2$ and 84% $N_2$ into the jar. Inocula were prepared by diluting the overnight Brian Heart infusion (Oxoid, Basingstoke, UK) cultures in buffered saline to a density of 0,5 on the McFarland turbidity scale and diluted 40-fold before inoculating. Plates were seeded with approximately $1\times10^5$ CFU with a Steers inoculum. Control plates of both media without the product were inoculated at the end of the procedure. All plates were incubated at 37° C.

under micro-aerobic atmosphere. Readings were performed after 48 h. The MIC was recorded as the lowest concentration that completely inhibited bacterial growth, thus disregarding faint hazes of growth or single colonies.

TABLE 1

MIC (%) value of the MCFA product ($C_6$-$C_8$) on different *Campylobacter* strains

| Strain | Number | MIC |
|---|---|---|
| C. jejuni | ATCC 33560 | 0.01 |
| C. coli | ATCC 33559 | 0.01 |
| C. jejuni | KH-03-1 | 0.01 |
| C. jejuni | KH-03-2 | 0.01 |
| C. jejuni | KH-03-3 | 0.005 |
| C. jejuni | KH-03-4 | 0.01 |
| C. jejuni | KH-03-5 | 0.01 |
| C. coli | KH-03-6 | 0.005 |

The results in Table 1 clearly illustrate that specific $C_6$ and $C_8$ MCFA in the used concentrations have an inhibiting effect at pH 7.2 on *C. jejuni* and *C. coli*. The bacterial strains were killed.

Example 2

Influence of MCFA on *Campylobacter*, *Salmonella*, *Escherichia* and *Enterococcus*

Three tenfold dilutions of a 5% MCFA blend ($C_6$ and $C_8$) (stored at 7° C.) were prepared in distilled water. $C_6$ and $C_8$ were used in equal amounts (50/50) by weight. The 5% suspension thus contained 2.5% $C_6$ and 2.5% $C_8$. To obtain the desired concentrations, 1.5, 0.75 and 0.36 ml of these dilutions were pipetted in petri dishes and carefully mixed with 15 ml molten growth medium. The Mueller-Hinton II medium (BBL) with a pH of 7.2 was used.

Preserved strains (*Campylobacter jejuni* ATCC 33560 and *Salmonella typhimurium* DAB 76. Two antibiogram control strains, *Enterococcus faecalis* ATCC 29212 and *Escherichia coli* ATCC 25923) were grown in Brian Heart infusion broth. Inocula were prepared from overnight 16 to 26 h old broth cultures incubated at 37° C. These were obtained by suspending growth in sterile saline in a photometer adapted for McFarland scale measurements (bioMérieux). Solutions matching 0.5 McFarland were diluted 10-fold in saline and inoculated on the MCFA and control plates using a Denley Multipoint Inoculator (Mast). In this way approximately 10,000 colony forming units of each strain was inoculated on the plates. All plates were incubated at 37° C. Incubation was performed under aerobic, under micro-aerobic (by evacuating 80% of the normal atmosphere and introducing a gas mixture of 8% $CO_2$, 8% $H_2$ and 84% $N_2$ into the jar) or anaerobic (in a $H_2$+$CO_2$) conditions. Readings were performed after 48 h.

The minimal inhibitory concentration (MIC) was recorded as the lowest concentration that completely inhibited growth, thus disregarding faint hazes of growth or single colonies. Results are shown in table 2.

TABLE 2

MIC (%) of MCFA against the food-born pathogens *Campylobacter* and *Salmonella*

| | Micro-organism | | | |
|---|---|---|---|---|
| | E. coli* | E. faecalis* | S. typhimurium | C. jejuni |
| Aerobic conditions | 0.025 | 0.012 | 0.025 | — |
| Micro-aerobic conditions | 0.025 | 0.012 | 0.025 | 0.0025 |
| Anaerobic conditions | 0.025 | 0.005 | 0.025 | <0.0012 |

*control strains

The *Campylobacter* strain tested did not grow under aerobic conditions. The MIC of all both food-born pathogens ranged from 0.025% to less than 0.0012% of MCFA. This indicates that the supply of specific MCFA provides a strong inhibitory effect on food born pathogens, such as *Campylobacter* and *Salmonella*. Growth of both strains is surprisingly inhibited and the respective micro-organisms are killed by the MCFA. This indicates that $C_6$ and $C_8$ MCFA in the applied amounts are particularly useful for control these types of food-born pathogens. *Campylobacter* is ten times more sensitive, compared to *Salmonella*.

Example 3

Influence of MCFA ($C_6$-$C_8$) on *Salmonella*-Infected Pigs 43 piglets were divided into 3 groups: MCFA ($C_6$-$C_8$) (group A, n=16), a positive control group (group B, n=16) and a negative control group (group C, n=11). The trial started at weaning and lasted for 42 days after which all animals were euthaniased. In each pen of group A and B, 2 of the 4 piglets were experimentally inoculated with *Salmonella* ser. *typhimurium* before putting them with 2 non-infected piglets. Inoculation took place three days after weaning. MCFA ($C_6$ and $C_8$) supplemented feed (see feeds 1 and 2 below) was given from 3 days before inoculation until the end of the trial. $C_6$ and $C_8$ were used in equal amounts (50/50) by weight. Clinical score was measured 2 times a week by the same veterinarian. Therefore, following codes were given to the piglets:

0=normal alert pig responding to the observer entering the pen, normal behaviour, evades handling 1=dull, evades handling but only walked short distances, did not exhibit many normal behaviour activities, could lay down while observer was in the pen 2=very dull, required prodding to move, preferred to lie Faeces score was also measured 2 times a week by the same veterinarian. Therefore, following codes were given to the piglets:

0=normal

1=soft faeces (or cow-pat consistency)

2=diarrhoea

Further, performance parameters including average daily gain (ADG) and feed intake (FI) were investigated. Feed conversion ratio (FCR) was calculated for the total group. Finally, mortality rate was measured.

Weaning feed was distributed from weaning till two weeks after weaning and was the following:

Feed 1: Control weaning feed

Feed 2: Control weaning feed+0.3% MCFA ($C_8$ and $C_8$)

Starter feed was distributed from day 15 after weaning till 7 weeks after weaning, and was the following:

Feed 3: Control starter feed
Feed 4: Control starter feed+0.2% MCFA ($C_6$ and $C_8$)

The piglets were fed ad libitum from arrival of the piglets and during the whole trial period (=preventive feeding programme).

Infection of the piglets occurred as follows: the piglet received 1 ml of a TSB solution containing $1.9 \times 10^9$ CFU's *Salmonella* ser. *Typhimurium*, which was a field strain from Belgium. This solution was solved in 4 ml of milk, which was given orally to each piglet. The dose was based on literature data (Wood et al., 1989).

Above experimental design is illustrated in Table 3. The trial was blinded for feed formulation, feed allocation, data collection and statistical analysis. Consequently, it was a triple blind randomised trial. Zootechnical performances are given in Table 4.

TABLE 3

Piglet-, infection- and feed distribution in the experimental farm

| | | | | Number of | | |
|---|---|---|---|---|---|---|
| Battery* | Group | Feed Weaning | Starter | Pens occupied/ total pens | Animals | Infected animals |
| 1 | C | 1 | 3 | 3/4 | 11 | 0 |
| 2 | B | 1 | 3 | 2/4 | 8 | 4 |
| 3 | B | 1 | 3 | 2/4 | 8 | 4 |
| 7 | A | 2 | 4 | 2/4 | 8 | 4 |
| 8 | A | 2 | 4 | 2/4 | 8 | 4 |

*Battery 4 was used for infection of the animals. Afterwards, the infected animals were putted together with non-infected ones at day 0. This way, the table summarises the situation at day 0.

TABLE 4

Zootechnical performances of the piglets in the *Salmonella* trial

| | | Group A MCFA ($C_6$-$C_8$) | Group B Positive control | Group C Negative control |
|---|---|---|---|---|
| Daily growth (g/d) | Total group | 337 +/− 188 | 213 +/− 115 | 293 +/− 148 |
| Feed conversion | Total group | 1.58 | 1.80 | 1.57 |
| Mortality (%) | Non-infected piglets | 18.8 | 25 | 9.1 |
| | Infected piglets | 25 | 50 | 0 |
| | Total group | 18.8 | 37.5 | 9.1 |

This example illustrates that $C_6$ and $C_8$ MCFA have an influence on ADG and FCR. Piglets in the MCFA ($C_6$/$C_8$) group had a numerically higher ADG than in the positive control group. ADG in group A, B and C was 337±188, 213±115 and 293±148 g/day, respectively. Standard deviation is high because of the high mortality rate in the different groups. FCR was similar in group A compared to group C, while the feed conversion in group B was higher. The higher feed conversion ratio in group B is due to the higher feed conversion in the weaning phase. Mortality was lowest in group C, while in group B the mortality was highest. Especially in the infected piglets, the difference between the MCFA ($C_6$-$C_8$) group (A) and the positive control group (B) was obvious. In 10.2% of cases, animals in group A had a clinical score higher than 0. For group B 19.0% and for group C 1.5% (p>0.05). The average number of cases of diarrhoea for group A, B and C was 17.9%, 30.0% and 10.0% respectively (p>0.05).

The results show that the mortality rate can be decreased by addition of MCFA ($C_6$ and $C_8$) to the feed. The decrease in mortality rate after addition of MCFA ($C_6$ and $C_8$) can be explained by the better clinical and faecal parameters of the animals.

MCFA ($C_6$ and $C_8$) are able to improve the ADG of the piglets after *Salmonella* infection. This is likely caused by the better clinical condition and the better gastrointestinal health, as proved by the improved faeces score. It is remarkable that even a better ADG is obtained for animals receiving MCFA ($C_6$ and $C_8$) in relation to animals in the negative control. This can be explained by its positive effect on villi status, what results in higher nutrient uptake from the gastrointestinal lumen.

MCFA ($C_6$ and $C_8$) completely restore FCR (feed conversion ratio), which increases very quickly after *Salmonella* infection. After infection and when no feed additives are present, the clinical and physical condition of the animals are very bad, what is reflected in a high feed conversion ratio. Based on the results, *Salmonella* infection has only influence on FCR in the weaning phase. This means that at the beginning of the starter period, the animal is already well recovered from its *Salmonella* infection. This is also reflected in ADG in the starter period for the positive control. Addition of MCFA ($C_6$ and $C_8$) in starter period has therefore no influence on FCR.

From above results, it can be concluded that MCFA ($C_6$ and $C_8$) provide a very effective alternative for growth promoters (antibiotics) for controlling *Salmonella* infection in pigs.

Example 4

Influence of Different MCFA Blends on *Salmonella* Survival

Three tenfold dilutions of a 10% suspension of four products:

1. 22.5% $C_8$/22.5% $C_{10}$
2. 45% $C_8$
3. 22.5% $C_6$/22.5% $C_8$
4. 45% $C_6$ (stored at 7° C., before use) were prepared in distilled water.

To obtain the desired concentrations, 1.5, 0.75 and 0.36 ml of these dilutions were pipetted in petri dishes and carefully mixed with 15 ml molten growth medium. The used medium was "de Man, Rogosa, Sharpe (MRS) medium" (Oxoid, CM361) with a pH of 6.2. The strains (*Salmonella* ser. *Typhimurium* DAB 76 and one wild *Salmonella* strain isolated from pork, serotyped at the W.I.V. institute, Brussels) were grown in BHI for 24 h under aerobic conditions. Inocula were prepared by diluting the overnight Brian Heart infusion (Oxoid, Basingstoke, UK) cultures in buffered saline to a density of 0,5 on the McFarland turbidity scale and diluted 40-fold before inoculating. Plates were seeded with approximately $1 \times 10^5$ CFU with a Steers inoculum. Control plates of both media without the product were inoculated at the end of the procedure. All plates were incubated at 37° C. under appropriate atmosphere. Readings were performed after 48 h. The MIC was recorded as the lowest concentration that completely inhibited growth, thus disregarding faint hazes of growth or single colonies. Results are given in table 5. From table 5, it can be concluded that $C_6$ as well as $C_6$/$C_8$ blends are effective ones

TABLE 5

MIC (%) of different MCFA blends against
the food-born pathogen *Salmonella*

| | | Blend | | | |
|---|---|---|---|---|---|
| | | 1 | 2 | 3 | 4 |
| Salmonella Typhimurium | DAB 76 | 0.025 | 0.01 | 0.01 | 0.01 |
| Salmonella Typhimurium | KH-03-7 | 0.025 | 0.025 | 0.01 | 0.01 |

Example 5

Influence of Different MCFA Blends on *E. Coli* Survival

In this example the anti-microbial activity of $C_6$ and/or $C_8$ and/or $C_{10}$ MCFA against *E. coli* K88 was evaluated. The preparation of the test solution was as follows. to 1 kg feed (composition Table 6) an exactly determined quantity of *E. coli* K 88 was added. Subsequently, a suspension of 20% feed and 80% physiologic solution (0,85% saline) was created. To simulate the 20%-suspension in a gastric environment, a pH of 4.0 with 0.1 N HCl was established.

TABLE 6

Experimental feed composition

| Raw Material | Quantity (g) |
|---|---|
| Wheat | 500 |
| Corn, pressure cooked | 200 |
| Soya ful fat beans Danex | 150 |
| Herringmeal | 50 |
| Whey powder | 70 |
| Premix | 30 |

The acidified suspension was distributed in samples of 100 ml. Test substances were added in different concentrations as mentioned in table 7.

TABLE 7

Concentration range of the different test substances

| | Concentration (%) | | | |
|---|---|---|---|---|
| Caproic acid ($C_6$) | 0.06 | 0.125 | 0.25 | 0.50 |
| Caprylic acid ($C_8$) | 0.06 | 0.125 | 0.25 | 0.50 |
| Capric acid ($C_{10}$) | 0.06 | 0.125 | 0.25 | 0.50 |

A microbial count at t=0 was executed. Samples were incubated during 3 h at 37° C. Samples were removed after 3 h and pH and microbial count were determined. The *E. coli* strains were counted on a Coli ID medium (Bio Mérieux, 42017).

The planned observations were:
 a. Microbial count of control sample (blank) on t=0
 b. Microbial count of control sample (blank) and treatments on t=3 h.

Table 8 depicts the calculated results proving the effectiveness of the anti-microbial effectiveness in the stomach of the different MCFA

TABLE 8

Antimicrobial effect of $C_6$, $C_8$ and $C_{10}$

| | Log (CFU/g) | |
|---|---|---|
| Test substance | T = 0 h | T = 3 h |
| Blank | 5.293 | 5.449 |
| $C_6$ 0.06% | 5.708 | 4.160 |
| $C_6$ 0.125% | 5.700 | Total inhibition |
| $C_6$ 0.250% | 4.920 | Total inhibition |
| $C_6$ 0.500% | Total inhibition | Total inhibition |
| $C_8$ 0.06% | 5.649 | Total inhibition |
| $C_8$ 0.125% | 5.415 | Total inhibition |
| $C_8$ 0.250% | Total inhibition | Total inhibition |
| $C_8$ 0.500% | Total inhibition | Total inhibition |
| $C_{10}$ 0.06% | 6.964 | 6.854 |
| $C_{10}$ 0.125% | 6.927 | 6.707 |
| $C_{10}$ 0.250% | 6.966 | 4.708 |
| $C_{10}$ 0.500% | 6.816 | Total inhibition |

From table 8, it can be concluded that $C_6$, $C_8$ and $C_{10}$ provide antimicrobial actions against *E. coli*.

Example 6

Effect of $C_8$ Versus $C_{10}$ on the Zootechnical Performance of Pigs

In this example the effect of $C_8$ versus $C_{10}$ on the zootechnical performance of pigs was investigated. Following feeds were used:

Feed A: a negative control feed without antimicrobial growth promoter

Feed B: feed A containing 0.125% $C_{10}$

Feed C: feed A containing 0.125% $C_8$

Feed D: feed A containing 0.125% $C_8/C_{10}$ mixture (50/50 ratio)

During the whole trial the pigs were fed ad libitum. The piglets under study were 200 weaned barrows and sows, with an age of 28 days at weaning. Piglets were distinguished by their ear tag and weighed individually. They were allocated randomly to the different feed groups, but the average initial weight per group was equal. The animals were followed during 2 weeks (starter period). Four groups of 50 animals were monitored. Following parameters were followed: feed intake per group, individual piglet weight and feed conversion per group. Results are given in table 9.

TABLE 9

Comparative effect of $C_8$ versus $C_{10}$ on
the zootechnical performance of pigs

| | Feed | | | |
|---|---|---|---|---|
| | A | B | C | D |
| Daily feed intake (g/pig/d) | 566 | 569 | 665 | 603 |
| Daily gain (g/pig/d) | 309 | 316 | 384 | 336 |
| Feed conversion | 1.83 | 1.80 | 1.73 | 1.80 |

In these experiments, best daily gain, feed conversion and feed intake were obtained after supplying $C_8$ to the feed. However the supply of $C_{10}$ as such, or in combination with $C_8$ also provided better effects than the control treatment.

Example 7

Effect of MCFA on Growth and Survival of *Campylobacter* sp. Isolated from Poultry Caecum In this example, the MIC values of different MCFA against *Campylobacter* sp. isolated from poultry caecum were determined.

Three tenfold dilutions of a 10% suspension of three types of MCFA's ($C_6$, $C_8$ and $C_{10}$) were prepared in distilled water. To obtain the desired concentrations, 1.5, 0.75 and 0.36 ml of these dilutions were pipetted in petri dishes and carefully mixed with 15 ml molten growth medium. A suitable fermentation medium was used with a pH of 5.0.

Isolated *Campylobacter* strains were grown in suitable fermentation medium and incubated at 37° C. under microaerobic conditions by evacuating 80% of the normal atmosphere and introducing a gas mixture of 8% $CO_2$, 8% $H_2$ and 84% $N_2$ into the jar. Inocula were prepared by diluting the cultures in buffered saline to a density of 0.5 on the McFarland turbidity scale and diluted 40-fold before inoculating. Plates were seeded with inoculum. Control plates of media without the product were inoculated at the end of the procedure. All plates were incubated at 37° C. under appropriate atmosphere. Readings were performed after 48 h. *Campylobacter* was counted after incubation.

Figure 2:
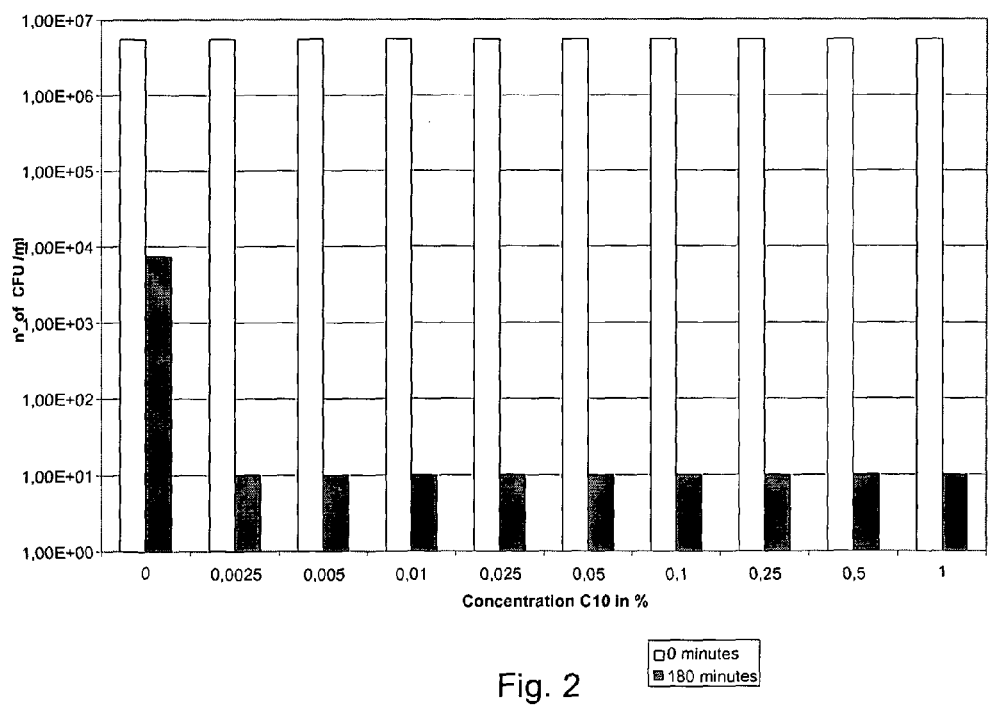
Figure 3:
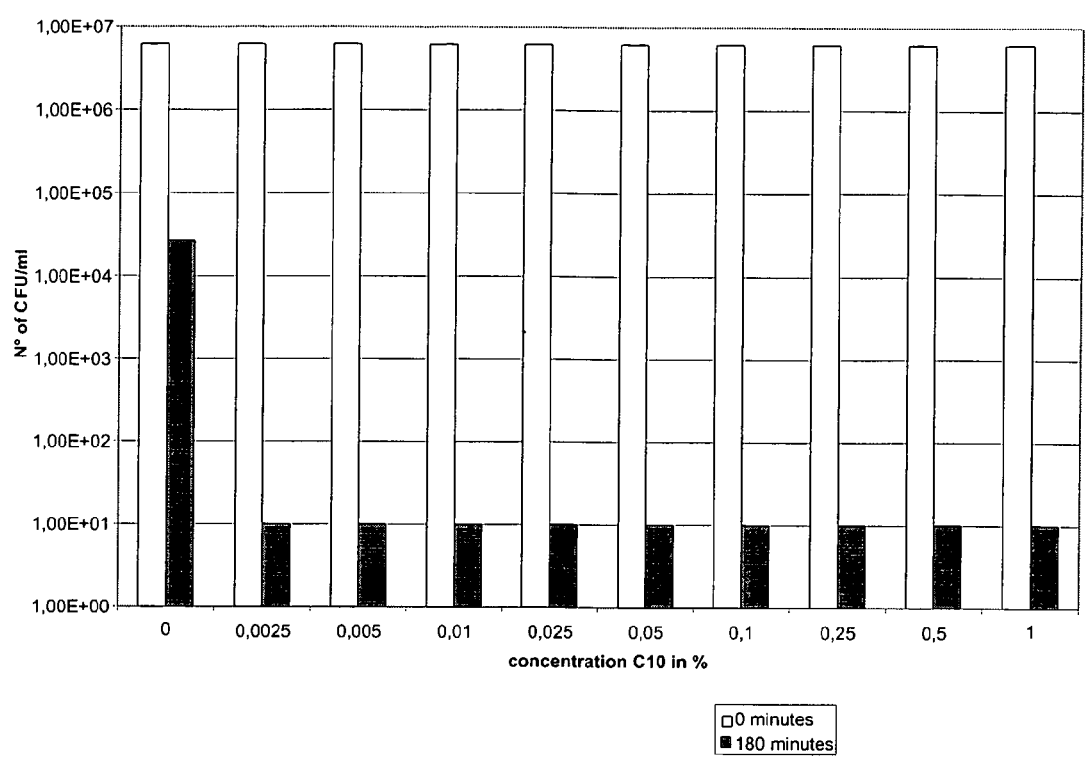
Figure 4:
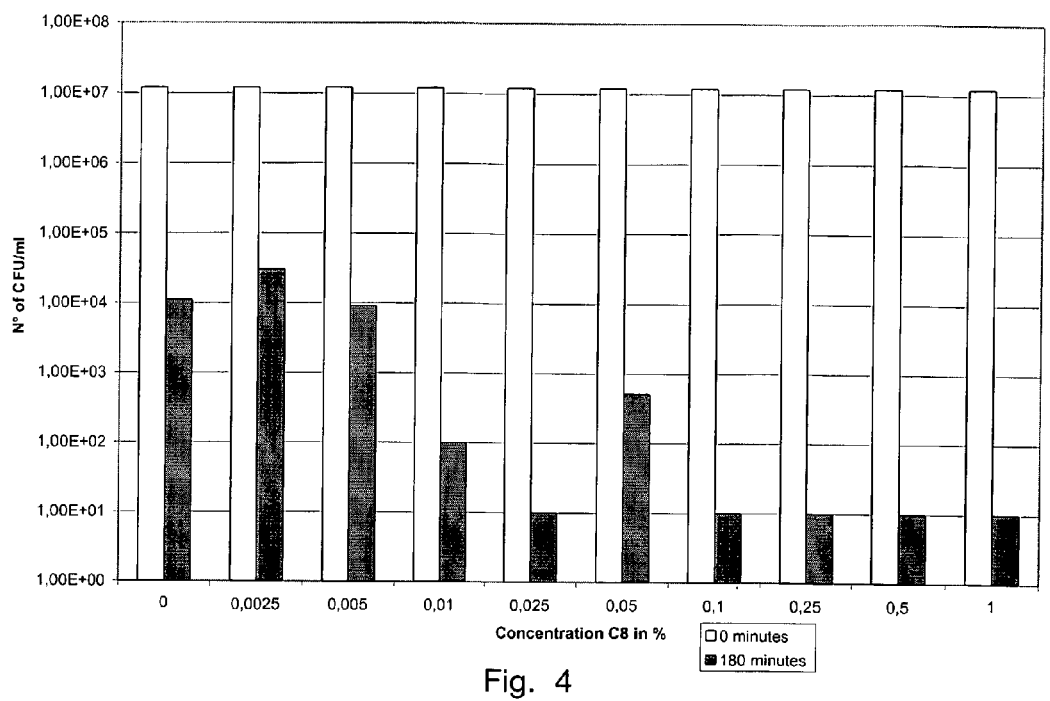
FIGS. 4 to 6 illustrate the effect of $C_8$ MCFA on growth and survival of different *Campylobacter* sp. strains isolated from poultry caecum.
Figure 5:
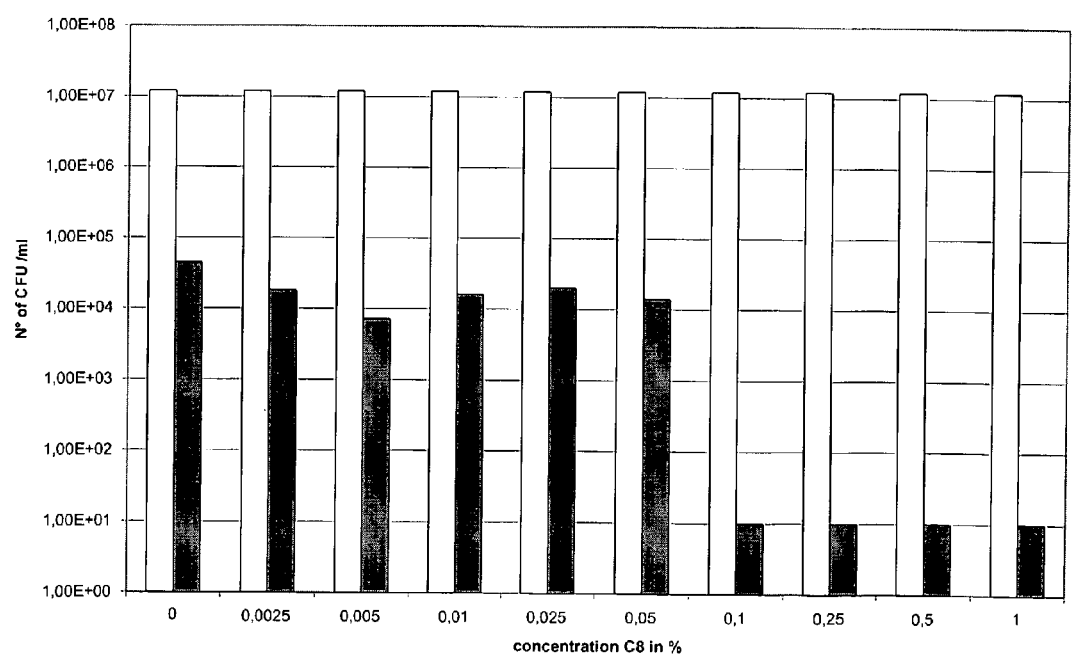
Figure 6:
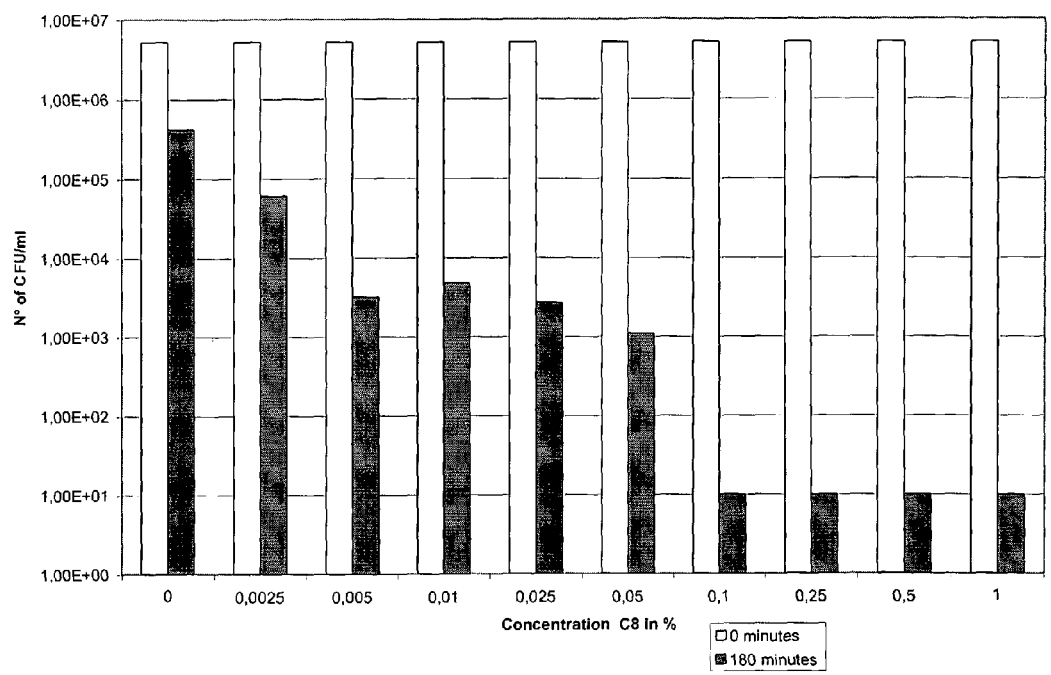
Figure 7:
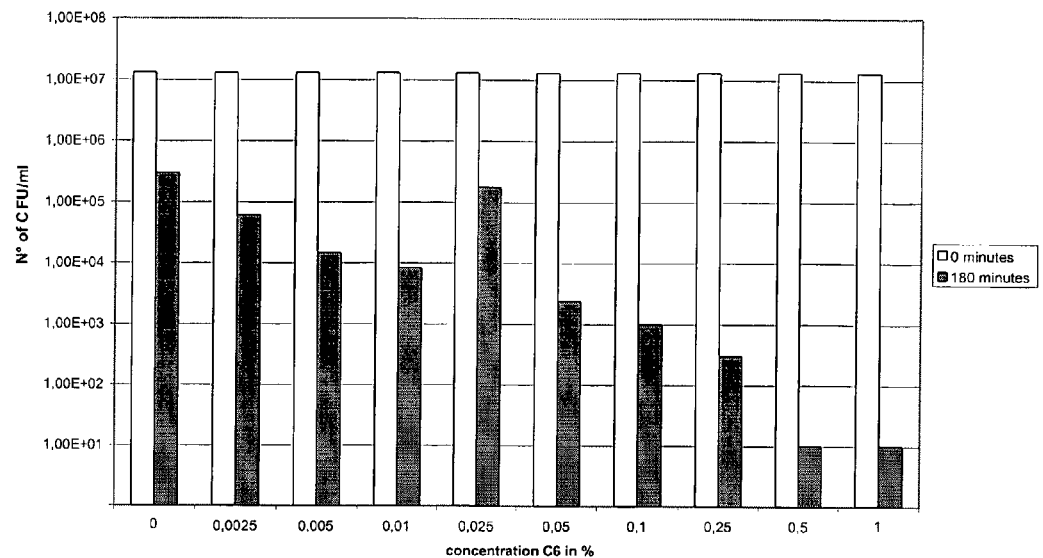
FIGS. 7 to 9 illustrate the effect of $C_6$ MCFA on growth and survival of different *Campylobacter* sp. strains isolated from poultry caecum.
Figure 8:
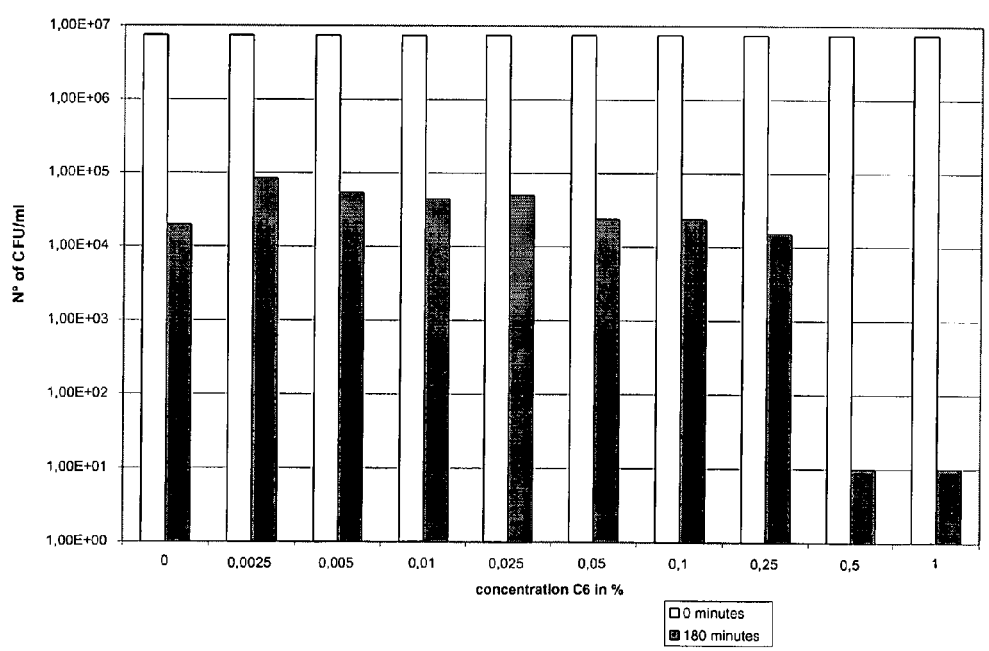
Figure 9:
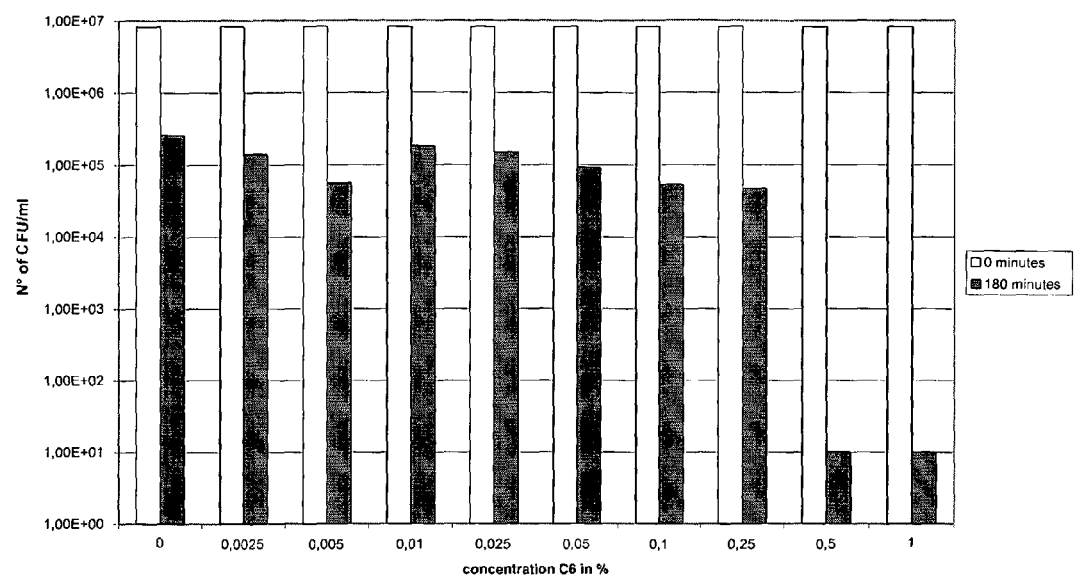

Results of the experiments using $C_{10}$ MCFA are shown in FIGS. 1-3. Results of the experiments using $C_8$ are shown in FIGS. 4-6. Results of the experiments using $C_6$ are shown in FIGS. 7-9. These figures represent the number of colony forming units (CFU)/ml of *Campylobacter jejuni* VC 5 strain (FIGS. 1, 4, 7), *Campylobacter jejuni* VC 6 strain (FIGS. 2, 5, 8), and *Campylobacter jejuni* VC 7 strain (FIGS. 3, 6, 9) at various concentrations of MCFA and at two different time points (0 and 180 minutes).

Results of these experiments showed that at the tested concentrations $C_6$, $C_8$ as well as $C_{10}$ MCFA show antimicrobial activities against different *Campylobacter* strains. It was also shown that under the test conditions of this experiment $C_{10}$ MCFA showed a stronger antimicrobial effect compared to $C_8$, while $C_8$ showed a stronger antimicrobial effect compared to $C_6$ MCFA on the tested *Campylobacter* strains.

References

BARTON, M. D. (1998). Does the use of antibiotics in animals affect human health. Aust. Vet. J., 76, 177.

CORRY, J. E. L. AND ATABAY, H. I. (2001). Poultry as source of *Campylobacter* and related organisms. J. Appl. Microbiol., 90, 96S-114S.

DUPONT, H. L. AND STEELE, J. H. (1987). Use of antimicrobial agents in feeds: implications for human health. Rev. Infect. Dis., 9, 447.

FRIEDMAN, C. R., NEIMANN, J., WEGENER, C. AND TAUXE, R. V. (2000). Epidemiology of *Campylobacter jejuni* infections in the United States and other industrialized nations. In: NACHAMKIN, I. AND BLASER, M. J. (eds.). *Campylobacter*. Washington, American Society for Microbiology, 121-138.

GUILLOT, J. F. (1989). Apparition et evolution de la resistance bactériènne aux antibiotiques. Ann. Rech. Vét., 20, 3.

KABARA, J. (1978). Fatty acids and derivatives as antimicrobial agents—a review. In: KABARA, J. (ed.). The pharmaceutical effects of lipids, AOCS, Champaign, I11, USA, 1.

NACHAMKIN, I., ALLOS, B. M. AND HO, T. (1998). *Campylobacter* species and Guillain-Barré syndrome. Clin. Microbiol. Rev., 11, 555-567.

NEWELL, D. G. AND NACHAMKIN, I. (1992). Immune responses directed against *Campylobacter jejuni*. In: NACHAMKIN, I., BLASER, M. J. AND TOMPKINS, L. S. (eds.). Current status and future trends. Washington, American Society for Microbiology, 201-206.

NEWELL, D. G. AND WAGENAAR, J. A. (2000). Poultry infections and their control at the farm level. In: NACHAMKIN, I. AND BLASER, M. J. (eds.). *Campylobacter*. Washington, American Society for Microbiology, 497-509

OBERHELMAN, R. A. AND TAYLOR, D. N. (2000). *Campylobacter* infections in developing countries. In: NACHAMKIN, I. AND BLASER, M. J. (eds.). *Campylobacter*. Washington, American Society for Microbiology, 139-153

PRESCOTT, J. F. (1997). Antibiotics: miracle drugs or pig food. Can. Vet. J., 38, 763.

SCOTT, D. A., BAQAR, S., PAZZAGLIA, G., GUERRY, P. AND BURR, D. H. (1997). Vaccines against *Campylobacter jejuni*. In: LEVINE, M. M., WOODROW, G. C., KAPER, J. B. AND COBON, G. S. (eds.). New generation vaccines. New York, Marcel Dekker Inc., 885-896.

WOOD, R. L., POSPISCHIL, A. AND ROSE, R. (1989). Distribution of persistent *Salmonella Typhimurium* infection in internal organs of swine. American Journal of Veterinary Research, 50, 1015-1021.

The invention claimed is:

1. A method for treating intestinal microbial infections by *Campylobacter* sp. in animals and humans by administering to said animal or human a feed supplement containing medium chain fatty acids (MCFA) chosen from the group of caproic acid ($C_6$) and caprylic acid ($C_8$), salts, derivatives or mixtures thereof, whereby said MCFA are present in the feed supplement in a total amount by weight comprised between 0.01% and 5%.

2. The method according to claim 1, wherein said MCFA are used in a total amount by weight of 0.3% in the feed supplement.

3. The method according to claim 1, wherein the feed supplement comprises a mixture of caproic acid ($C_6$) and caprylic acid ($C_8$).

4. The method according to claim 1, wherein said composition further comprises capric acid ($C_{10}$), or salts, or derivatives thereof.

5. The method according to claim 4, wherein the feed supplement comprises a mixture of caproic acid ($C_6$) and capric acid ($C_{10}$).

6. The method according to claim 1, wherein the ratio of $C_6$ to $C_8$ in the feed supplement is comprised between 2:1 and 1:2.

7. The method according to claim 4, wherein the ratio of $C_8$ to $C_{10}$ in the feed supplement is comprised between 2:1 and 1:2.

8. The method according to claim 4, wherein the ratio of C6 to C10 in the feed supplement is comprised between 2:1 and 1:2.

9. The method according to claim 4, wherein the feed supplement comprises a mixture of caproic acid ($C_6$), caprylic acid ($C_8$) and capric acid ($C_{10}$).

10. The method according to claim 1, wherein the MCFA are used in the feed supplement as free MCFA, as mono-, di- and/or triglicerides, as $NH_4^+$—, $Na^+$—, $K^+$— and/or $Ca^{2+}$— salts or in the form of an emulsion.

11. The method according to claim 4, wherein the feed supplement comprises a mixture of caprylic acid ($C_8$) and capric acid ($C_{10}$).

\* \* \* \* \*